US005571104A

United States Patent [19]

Li

[11] Patent Number: 5,571,104
[45] Date of Patent: Nov. 5, 1996

[54] SURGICAL ANCHOR AND METHOD FOR USING THE SAME

[75] Inventor: Lehmann K. Li, Milford, Conn.

[73] Assignee: Mitek Surgical Products, Inc., Westwood, Mass.

[21] Appl. No.: 468,053

[22] Filed: Jun. 6, 1995

Related U.S. Application Data

[62] Division of Ser. No. 75,168, Jun. 10, 1993, Pat. No. 5,505,735.

[51] Int. Cl.[6] .................................................. A61B 17/00
[52] U.S. Cl. .............................. 606/72; 606/75; 606/232
[58] Field of Search ................................. 606/72, 73, 74, 606/75, 76, 77, 219, 220, 232

[56]  References Cited

U.S. PATENT DOCUMENTS

| | | | |
|---|---|---|---|
| 5,156,616 | 10/1992 | Meadows et al. | 606/232 |
| 5,236,445 | 8/1993 | Hayhurst et al. | 606/232 |
| 5,356,413 | 10/1994 | Martins et al. | 606/75 |
| 5,372,599 | 12/1994 | Martins | 606/232 |
| 5,505,735 | 4/1996 | Li | 606/72 |

*Primary Examiner*—Gary Jackson
*Assistant Examiner*—Sonya Harris-Ogugua
*Attorney, Agent, or Firm*—Pandiscio & Pandiscio

[57]  ABSTRACT

An anchor for attaching an object within a tunnel extending through a workpiece such as a bone or a bone-like structure, and a method for using the same. The anchor includes a body and a plurality of barbs located in circumferentially spaced relation about the body. The barbs are formed of a material which may be elastically deformed from a normal configuration wherein the outer ends of the barbs extend radially outwardly of the body toward a configuration wherein the barbs are located generally parallel to the longitudinal axis of the body. A diametrical opening in the front portion of the anchor is provided for engagement by a length of cord-like material such that the anchor may be pulled into a bone tunnel, and an opening in the rear portion of the anchor is provided for attaching either a ligament, tendon or the like to the anchor, or for grasping a bone plug or similar rigid object attached to a free end of the ligament, tendon or the like.

8 Claims, 7 Drawing Sheets

SURGICAL ANCHOR AND METHOD FOR USING THE SAME

This is a division of U.S. application Ser. No. 08/075,168, filed Jun. 10, 1993, now U.S. Pat. No. 5,505,735 Apr. 09, 1996 for Surgical Anchor And Method For Using The Same.

FIELD OF THE INVENTION

The present invention relates generally to fastening devices. More particularly, the invention relates to devices for attaching portions of objects within tunnels formed in bones or bone-like structures, and to methods for using the same.

BACKGROUND OF THE INVENTION

The complete, or partial, detachment of ligaments, tendons or other soft tissues from their associated bones within the body is a relatively commonplace injury, particularly among athletes. Such injuries generally result from excessive stresses being placed on these soft tissues. For example, a tissue-detaching injury may occur as the result of an accident such as a fall, overexertion during a work-related activity, during the course of an athletic event, or in any one of many other situations and/or activities.

In the case of a partial detachment, commonly referred to under the general term "sprain", the injury will frequently heal itself, if given sufficient time, and if care is taken not to expose the injury to any undue or extraordinary stress during the healing process. If, however, the ligament or tendon is completely detached from its associated bone or bones, or if it is severed as the result of a traumatic injury, partial or permanent disability may result. Fortunately, a number of surgical techniques exist for re-attaching such detached tissues and/or completely replacing severely damaged tissues.

One such technique involves the re-attachment of the detached tissue using "traditional" attachment devices such as metal staples, sutures over buttons and cancellous bone screws. Such "traditional" attachment devices have also been used to attach tendon or ligament substitutes (often formed of autogenous tissue harvested from elsewhere in the body) to the desired bone or bones.

Another technique is described in detail in U.S. Pat. No. 4,950,270 entitled "Cannulated Self-Tapping Bone Screw" issued Aug. 21, 1990 to Bowman et al. This patent is specifically incorporated herein by reference. In this technique, an anterior cruciate ligament in a human knee, for example, is replaced and/or repaired by forming bone tunnels through the tibia and/or femur at the points of normal attachment of the anterior cruciate ligament. A ligament graft, with a bone block (or plug) on at least one of its ends, is sized to fit within the bone tunnels. Suture is then attached to the outer end of each bone plug, and thereafter passed through the femoral and/or tibial bone tunnels. The femoral plug and/or the tibial plug is/are then inserted into the appropriate bone tunnel behind the suture. Subsequently, the suture is drawn tight (simultaneously in opposite directions, in cases where bone blocks are to be located in both a femoral bone tunnel and a tibial bone tunnel). This procedure positions the bone plug (or plugs) in the desired location, and imparts the desired degree of tension to the ligament or ligament substitute. Finally, while holding the bone blocks in position, a bone screw is inserted between each bone block and the side wall of its associated bone tunnel so as to securely lock the bone block in position using a tight interference fit.

Alternatives to the foregoing use of bone screws are also well known in the art. For example, in U.S. Pat. No. 5,147,362 entitled "Endosteal Ligament Fixation Device", issued Sep. 15, 1992 to E. Marlowe Goble, rearwardly extending flexible barbs or pins are attached to a bone plug (either directly or by a collar, cap or similar intervening element) for anchoring a bone plug within a bone tunnel. The disclosure of the foregoing U.S. Pat. No. 5,147,362 is specifically incorporated herein by reference.

In U.S. Pat. No. 4,997,433 entitled "Endosteal Fixation Stud and System", issued Mar. 5, 1991 to E. Marlowe Goble et al., a stud is disclosed for attachment to the outer end of the bone block. This stud includes a pair of spaced, forwardly projecting, flexible arms. One of these arms includes a substantially rigid, radially and rearwardly projecting portion disposed adjacent the arm's outer end. The stud is inserted through a bone tunnel ahead of a bone block to which it has been attached so that the projection may engage the outer surface of the bone adjacent the far end of the bone tunnel. This projection then acts to hold the bone block within the bone tunnel so long as rearwardly directed tension is maintained on the bone block. The disclosure of U.S. Pat. No. 4,997,433 is also specifically incorporated herein by reference.

Unfortunately, the repair devices and methods described above have not been uniformly successful. For example, tissue re-attachments effected using the aforementioned "traditional" fastening devices often cannot be maintained under even normal tensile loans.

Also, the use of sharp screws to create a locking interference fit between a bone plug and the side Wall of a bone tunnel introduces a number of problems. For one thing, there is always the possibility of damaging the ligament or repair material during insertion of the sharp screw. In addition, it can be difficult to maintain the desired tension on the ligament or repair material during insertion of the screw. Furthermore, the insertion of a bone screw requires that a twisting motion to be imparted to the screw. This twisting motion of the screw can in turn cause rotation of the bone block within the bone tunnel. If this occurs, undesirable twisting of the ligament may also occur.

The removal of such bone screws can also cause problems. In those cases in which the screw can be removed simply by unscrewing it in the usual manner, an undesirable hole is left in the bone. In many cases, however, the screw cannot simply be unscrewed from the bone to remove it. In these situations, the screw must typically be either forceably pulled out of the bone, or it must be removed by chipping away the surrounding bone. Both of these removal procedures can cause serious damage to the bone.

The foregoing attachment devices of U.S. Pat. Nos. 5,147,362 and 4,997,433 are also not totally satisfactory. This is because in the device of U.S. Pat. No. 5,147,362, the cross-sectional size of the bone tunnel must significantly exceed the cross-sectional size of the bone block due to the particular constructions utilized. This results in the bone block being spaced from the side wall of the bone tunnel, which can in turn delay assimilation of the bone block into the bone during healing. The device of U.S. Pat. No. 4,997,433, on the other hand, is limited to use in a particular method of re-attachment. Furthermore, undesirable binding may occur between the stud's projection and the side wall of the bone tunnel as the stud is forced through the bone tunnel.

Various types of suture anchors and anchors for attaching objects to bone are also well known in the art. A number of these devices are described in detail in U.S. Pat. Nos. 4,898,156; 4,899,743; 4,946,468; 4,968,315; 5,002,550; 5,046,513; and 5,192,303 (each of which is presently owned by Mitek Surgical Products, Inc. of Norwood, Mass., the assignee of this application). The disclosures of these patents are also specifically incorporated herein by reference.

OBJECTS OF THE INVENTION

Accordingly, one object of the present invention is to provide a surgical anchor useful in the repair and/or replacement of ligaments, tendons and similar elongated soft tissues.

Another object of the present invention is to provide a surgical anchor for holding a bone block in place in a bone tunnel, so that a piece of soft tissue attached to the bone block can be connected to a bone under tension.

Another object of the present invention is to provide a surgical anchor which avoids the danger of severing, twisting or otherwise damaging soft tissue repair or replacement material.

Another object of the present invention is to provide a surgical anchor which may be inserted into a tunnel formed in bone without causing serious damage to the surrounding bone.

Yet another object of the present invention is to provide a surgical anchor which is adapted to hold repair or replacement material in proximity to bone in a manner which promotes the growth of a permanent attachment therebetween.

And another object of the present invention is to provide a surgical anchor which may be drawn, rather than pushed, into a tunnel formed in bone.

Yet another object of the present invention is to provide a surgical anchor which includes simple and convenient means for attaching repair or replacement material or an object thereto.

And another object of the present invention is to provide an improved method for repairing and/or replacing ligaments, tendons or similar tissue by affixing an end of such tissue (or its replacement) within a tunnel extending through a bone or bone-like structure.

SUMMARY OF THE INVENTION

These and other objects are achieved by the use of the present invention, which comprises a novel surgical anchor and the use of the same. The novel surgical anchor generally comprises a body and a plurality of barbs.

The body comprises a longitudinal, axis, a front end, a rear end, a front portion adjacent the front end, a rear portion adjacent the rear end, and an outer surface. Connection means are associated with the front portion of the body for connecting the body to anchor pulling means. Attachment means are associated with the rear portion of the body for attaching a desired repair material (i.e., a piece of detached tissue, a replacement for detached tissue, a bone block, or some other object) to the body.

The connection means preferably comprises a bore extending transversely through the front portion of the body, and the anchor pulling means preferably comprises a length of strong suture, braided twine, wire or the like.

The attachment means may take any one of several forms. The specific form chosen will depend upon the nature of the repair material which is to be attached to the body, and upon the particular geometrical configuration chosen for the body itself. Accordingly, the attachment means may comprise an opening extending through the rear portion of the body. Alternatively, the attachment means may comprise a longitudinal slot extending into the rear end of the body.

In the latter slot alternative, the sections of the rear portion of the body forming the opposing sides of the slot may be pivotally attached to the front portion. In that case, the rear portion of the body may be opened to receive a bone block and then closed again so as to compressively retain the bone block in engagement with the anchor as the anchor is pulled into a bone tunnel. To help facilitate the block retention by the anchor, tines may be provided on the opposing side walls of the slot so as to bite into the bone block when the rear portion of the anchor is in its closed position.

In one particular embodiment of this alternative, the front portion of the body is formed in two pants which interlock in hinged, tongue-in-groove relation. Specifically, the tongue-defining part carries a first section of the anchor's rear portion which defines one of the opposing side walls of the slot. The groove-defining part carries a second section of the anchor's rear portion which defines the other of the opposing side walls of the slot. The hinge is elongated hollow pin frictionally engaging a transverse bore extending through the united tongue-defining and groove-defining parts. The lumen defined by the hollow pin constitutes the anchor's aforementioned connecting means.

The barbs are located in spaced circumferential relation to each other about the outer surface of the anchor's body. In the preferred embodiments, a plurality of identical longitudinal channels are located in substantially equally spaced circumferential relation to each other about the outer surface of the body. Each of these channels has a forward end located the same axial distance from the front end of the body. A barb extends outwardly and rearwardly from the forward end of each longitudinal channel to an outer end. The outer ends of the barbs are normally located radially outwardly of an axial projection of the maximum geometrical cross-section of the body, as taken perpendicular to its longitudinal axis. In addition, each barb is capable of being elastically deformed so that its outer end lies within the aforementioned axial projection of the maximum geometrical cross-section of the body. As a result of this construction, when the anchor is pulled into an appropriately sized bone tunnel using the aforementioned anchor pulling means, the anchor's barbs will engage the side wall of the bone tunnel and be deflected inwardly so as to allow the anchor to pass down the bone tunnel. At the same time, however, the anchor's barbs will prevent the anchor from being withdrawn from the bone tunnel in the direction of its entry.

In the method of the invention, a length of suture-like material is threaded through the transverse bore of the connection means, and the repair material is attached to the attachment means at the rear portion of the anchor body. In the case where the repair material constitutes soft tissue such as a ligament, tendon or the like, the connecting means may be in the form of a transverse opening extending through the anchor body, and the soft repair material may be attached directly to the anchor body by looping it through the transverse opening, or by attaching it to the opening via an intervening piece of suture or the like. In the case where the repair material constitutes a rigid element such as a bone plug block disposed at a free end of a ligament, tendon or the like, the connecting means may be in the form of a transverse opening and the repair material may be attached to the anchor body via an intervening piece of suture. Alternatively, in the case where the repair material constitutes a rigid element such as a bone block disposed at the free end of a ligament, tendon or the like, the connecting means may be in the form of a slot in the rear end of the body, and the rigid repair material may be positioned in the slot.

In any case, once the repair material has been attached to the anchor body, the free ends of the suture-like material extending through the connection means are inserted through a bone tunnel which is to receive the repair material. Thereafter, the anchor is pulled into and then along the bone tunnel by pulling on the free ends of the suture-like material. As this occurs, the anchor's barbs will yieldably engage the surrounding bone so as to permit the anchor, and hence the repair material, to be pulled along the bone tunnel until it reaches a desired position. At the same time, however, the anchor's barbs will prevent the anchor from being withdrawn from the bone tunnel in the direction from which it entered. In this way the repair material may be securely attached to the bone using the novel surgical anchor of the present invention.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
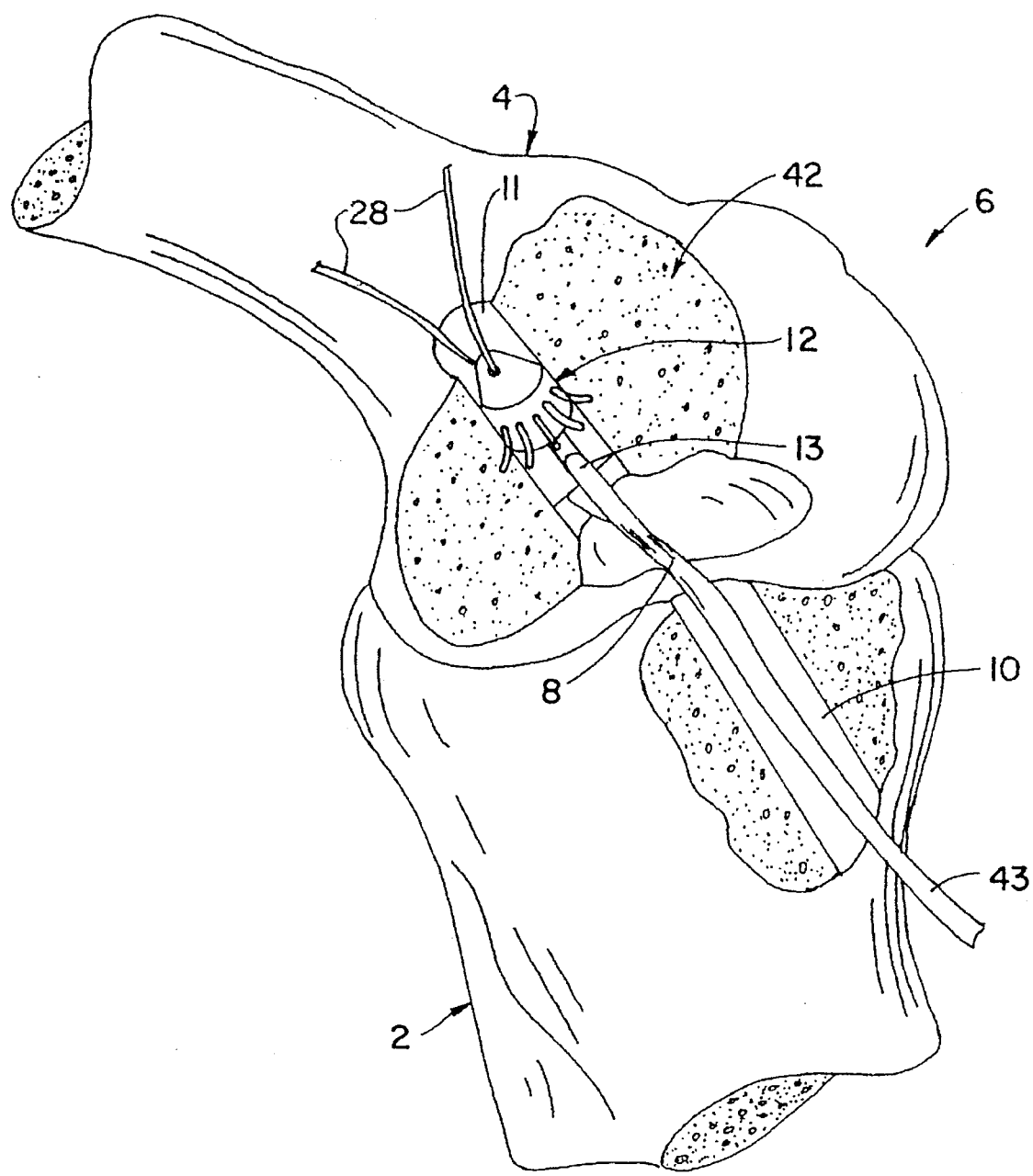
FIG. 1 is a side view in partial section showing a portion of a human femur bone and a portion of a human tibia bone adjacent a knee joint, each having a bone tunnel extending therethrough, and showing a first embodiment of a surgical anchor formed in accordance with the present invention, wherein the surgical anchor is attached directly to one end of a ligament.

Referring now to FIG. 1, there is shown a portion of a human tibia 2 and a portion of a human femur 4 at the point at which they meet to form a human knee joint, generally indicated at 6. The knee joint 6 is stabilized by a number of ligaments (not shown in the drawings for purposes of clarity) such as the patellar tendon, the quadriceps femuris tendon, the lateral and medial collateral ligaments, and the anterior and posterior cruciate ligaments. An anterior cruciate ligament graft 8 is shown extending through a tibial bone tunnel 10 and into a femoral bone tunnel 11. A surgical anchor 12, constituting a first embodiment of the present invention, is shown connecting ligament 8 to femur 4. Surgical anchor 12 is attached directly to the end 13 of ligament 8 which is located within femoral bone tunnel 11.

Figure 2:
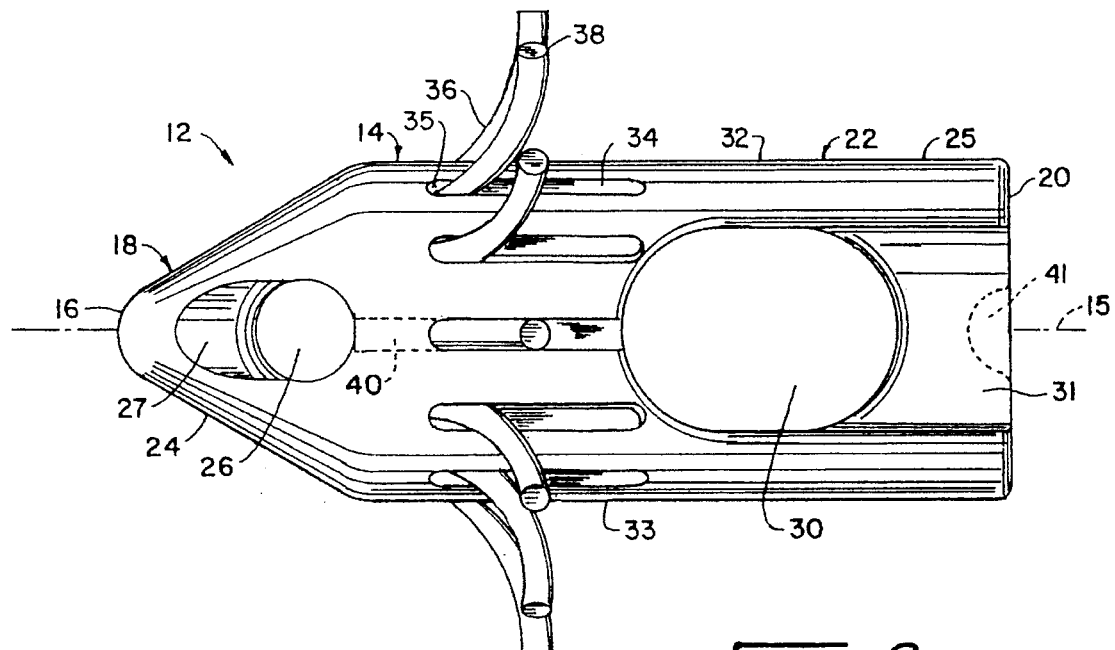
FIG. 2 is a side view of the surgical anchor shown in FIG. 1.
Figure 3:
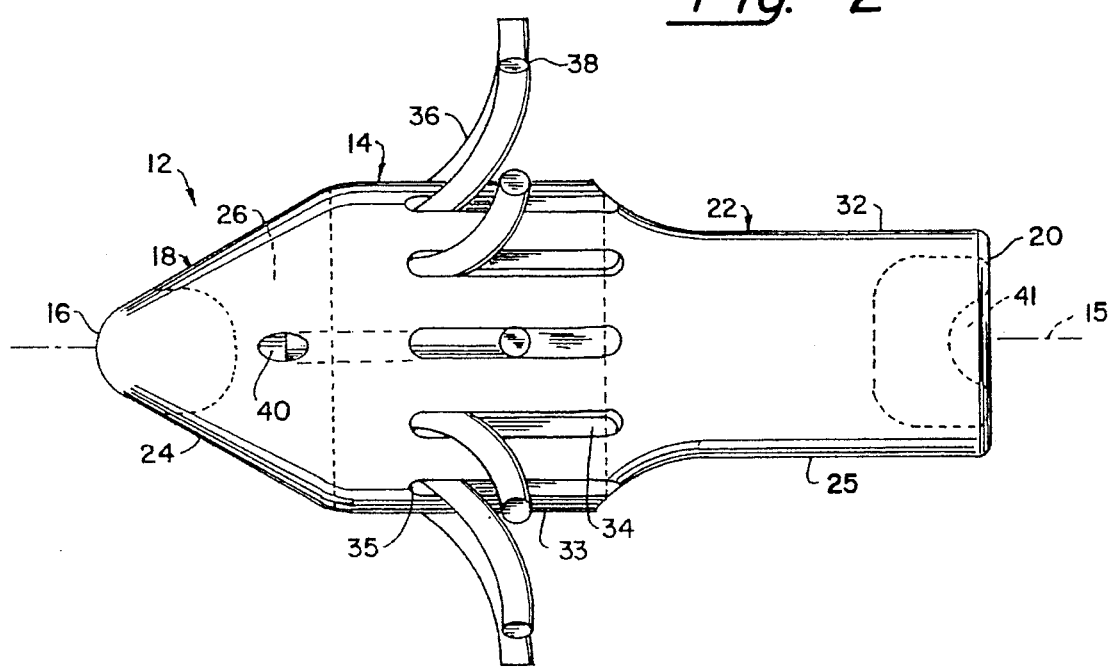
FIG. 3 is a side view of the surgical anchor shown in FIG. 2, wherein the anchor has been rotated 90° about its longitudinal axis.
Figure 4:
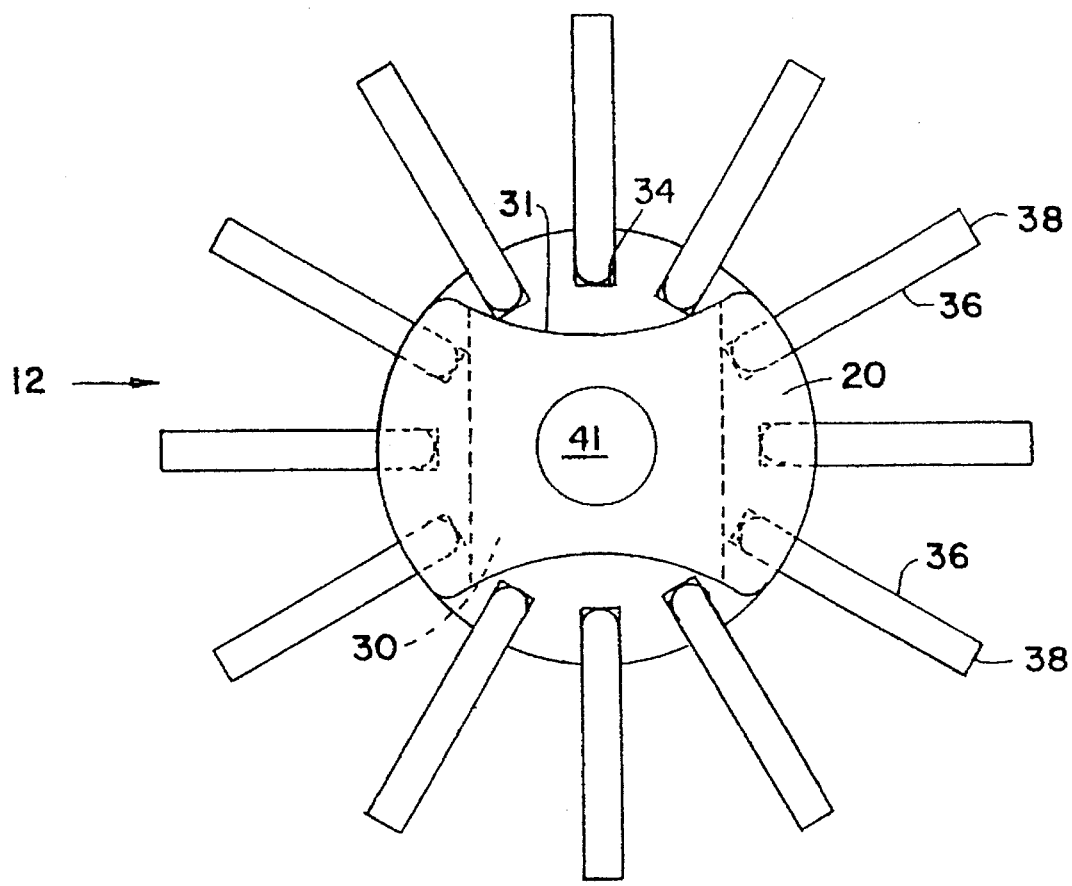
FIG. 4 is a rear view of the surgical anchor shown in FIG. 3.

Referring next to FIGS. 2–4, surgical anchor 12 comprises a body 14 having a longitudinal axis 15, a front end 16, a front portion 18 adjacent front end 16, a rear end 20, and a rear portion 22 adjacent rear end 20. The outer surface 24 of front portion 18 tapers gradually toward longitudinal axis 15 as it approaches front end 16. This provides body 14 with a generally forwardly pointed configuration. Rear portion 22 includes an outer surface 25. Body 14 is preferably formed out of 6AL-4V ELI titanium. It may, however, be formed out of any suitable biocompatible metal, biocompatible polymer or bioabsorbable material, all without departure from the present invention.

A bore 26 extends through front portion 18, perpendicular to longitudinal axis 15. Bore 26 is sized such that a strong suture 28 (FIG. 1), or some other suitable anchor pulling means, may be connected thereto for pulling anchor 12 in a forward axial direction. In addition, tapered grooves 27 extend forwardly from the openings of bore 26 onto outer surface 24. Grooves 27, combined with the rounding of the outer edges of bore 26, provide a smooth, substantially continuous surface against which the anchor pulling means 28 may bear. This reduces the chance of breaking the anchor pulling means 28 during deployment of the anchor.

The anchor's rear portion 22 includes an opening 30 extending transversely through body 14 adjacent its rear end 20. Opening 30 is preferably, but not necessarily, oriented substantially parallel to bore 26 in front portion 18. Opening 30 is sized to receive a loop of ligament, tendon or the like (FIG. 1), or a loop of suture which is in turn attached to a ligament, tendon or the like, or a loop of suture which is in turn attached to a bone block or plug, so as to attach the desired repair material to the anchor, as will hereinafter be discussed in further detail. Channels 31 extend rearwardly from the openings of aperture 30 onto outer surface 25. Channels 31 extend all the way to the anchor's rear end 20. These channels 31, combined with the rounding of the outer edges of opening 30, provide a smooth, substantially continuous bearing surface for the tissue, tissue substitute or suture material looped through opening 30. This reduces the chance of breaking or otherwise damaging the looped tissue, tissue substitute or suture material during anchor deployment. Furthermore, if desired, the rear section 32 of rear portion 22 which contains opening 30 may be flattened somewhat relative to the remainder of rear portion 22. This provides, in combination with channels 31, pathways for the looped tissue, tissue substitute or suture material passing through opening 30. Specifically, these pathways allow the looped material to extend along the flattened sides of rear section 32 without danger of the looped material being crushed between the anchor and the adjacent side wall of the bone tunnel.

The forward section 33 of rear portion 22 includes a plurality of equally circumferentially spaced longitudinal channels 34. Each channel 34 terminates in a forward end 35 located substantially the same axial distance from front end 16.

A plurality of barbs 36 extend outwardly and rearwardly from body 14, in spaced circumferential relation to each other. In the embodiment shown in FIGS. 1–4, one such barb 36 extends outwardly and rearwardly from the forward end 35 of each channel 34. Each barb 36 terminates in an outer end 38. Each outer end 38 is normally located radially outside the periphery of an axial projection of the maximum geometric cross-section of body 14, as taken perpendicular to longitudinal axis 15. At the same time, however, barbs 36 are formed out of an elastically deformable material such that outer ends 38 can be forced radially inwardly so as to be located within the periphery of an axial projection of the maximum geometric cross-section of body 14. On account of this construction, when an anchor 12 is inserted longitudinally into an appropriately sized bone tunnel, the outer ends 38 of barbs 36 will engage, and be deflected inwardly by, the side wall of the bone tunnel. This yieldable engagement of barbs 36 with the adjacent bone permits the anchor to be moved along the bone tunnel and then fixed securely in position, as will hereinafter be described in further detail.

In the preferred embodiment, barbs 36 are formed out of a pseudoelastic shape memory alloy of the type disclosed in U.S. Pat. No. 4,665,906 entitled "Medical Devices Incorporating SIM Alloy Elements", issued May 19, 1987 to Jervis, which patent is specifically incorporated herein by reference. By way of example, one such pseudoelastic shape memory alloy might be a nickel titanium alloy such as Nitinol, which is available from Flexmedics of Minneapolis, Minn., among others. The use of such a material, in combination with the normal orientation of the barbs relative to the anchor body, permits the barbs to initially deflect inwardly to the extent required to permit the anchor to move forward in the bone tunnel, yet still resiliently "spring back" toward their normal, outwardly projecting position so as to prevent the anchor from withdrawing back out the bone tunnel.

In the preferred embodiment, barbs 36 are formed as curved arcs extending outwardly from body 14 when in their normal, unstressed condition. Each barb forms an arc of approximately 90 degrees, with the length of the barbs being selected so that when one end is inserted into a longitudinal bore 40 extending forwardly from the forward end 35 of a slot 34, the other end extends the desired distance outwardly from body 14. In this respect it will also be appreciated that the forced fit of the curved barb within the straight bore 40, combined with the elastic memory of the barb, tends to hold the barb in place within the bore. At the same time, the sides of the associated channels 34 act to prevent the barb from twisting within the bore. The body of the anchor may also be crimped adjacent the bores 40 so as to further assure the locking engagement of the barbs to body 14, if desired. It is to be appreciated that the lengths (and widths) of barbs 36 and longitudinal channels 34 are carefully sized relative to one another, such that barbs 36 may be fully received in longitudinal channels 34 to the extent necessary when the barbs are deformed during anchor deployment.

An axial depression 41 is provided in rear end 20 of body 14. Depression 41 facilitates engagement of a thin push rod or similar device (not shown) with the anchor's rear end 20 in the event that it is desired to push the anchor into a bone tunnel. This application of a pushing force to the rear end of the anchor may be accomplished either in conjunction with, or as a substitute for, a pulling force applied to the front portion of the anchor via bore 26 and anchor pulling means 28.

Selected exemplary dimensions of two sizes (designated "A" and "B" respectively) of the surgical anchor shown in FIGS. 1–4 are set forth below for purposes of illustration:

|  | "A" | "B" |
| --- | --- | --- |
| Maximum diameter | 0.315 inches | 0.236 inches |
| Length | 1.50 inches | 0.750 inches |
| Diameter of bore 26 | 0.093 inches | 0.075 inches |
| Length of slot 30 | 0.268 inches | 0.195 inches |
| Width of slot 30 | 0.182 inches | 0.146 inches |
| Angle of taper of front portion 18 | 60 degrees | 60 degrees |
| Length of channels 34 | 0.193 inches | 0.193 inches |
| Width of channels 34 | 0.033 inches | 0.033 inches |
| Depth of channels 34 | 0.043 inches | 0.043 inches |
| Diameter of barbs 36 | 0.030 inches | 0.030 inches |
| Length of barbs 36 in straight configuration | 0.320 inches | 0.320 inches |
| Width of flattened section 32 | 0.220 inches | 0.160 inches |
| Depth of channels 31 | 0.030 inches | 0.020 inches |
| Number of barbs | 12 | 8 |
| Depth of depression 41 | 0.040 inches | 0.030 inches |

The use of surgical anchor 12 will now be described in the context of anchoring one end of an anterior cruciate ligament 8 (or its replacement) to a femur 4, as shown in FIG. 1.

A length of strong suture 28 is first threaded through bore 26 in the front portion of anchor 12. If desired, the free ends of the length of suture 28 may be secured together so as to facilitate grasping the free suture ends and applying a pulling force thereto. One end of the ligament or replacement material 8 is passed through opening 30 in the rear portion of the anchor and tied to itself so as to form a closed loop extending through opening 30 in the anchor. Alternatively, a length of suture may be looped through opening 30 and then connected to the ligament or replacement material 8 so as to connect the ligament or replacement material to the anchor. Or a bone block, affixed to the end 13 of a ligament or other elongate repair material 8, may be secured to opening 30 with a loop of suture.

Then suture 28, which is attached to the front end of anchor 12, is threaded through the tibial and femoral bone tunnels 10 and 11, respectively. Bone tunnels 10 and 11 are sized so as to be just slightly larger than the maximum diameter of anchor body 14, whereby the anchor's barbs 36 may engage the side walls of bone tunnels 10 and 11 as the anchor is pulled through the bone tunnels. Next, the free ends of suture 28 are pulled so as to draw anchor 12 (and its associated ligament or repair material 8) through tibial bone tunnel 10 and part way through femoral bone tunnel 11, until anchor 12 sits in the relatively soft cancellous region 42 of femur 4. At the same time, the free end 43 of the ligament or repair material 8 will extend out the end of tibial bone tunnel 10, as shown in FIG. 1. It will be understood that the generally forwardly pointed configuration of anchor 12 will facilitate its entry into and through the bone tunnels. It will also be understood that as the anchor is pulled along the bone tunnels, the anchor's outwardly extending barbs 36 will engage the side walls of the bone tunnels, deflecting inwardly as required so as to allow the anchor to pass down the bone tunnels. At the same time, however, these barbs 36 will resiliently engage the surrounding bone so as to prevent the anchor from being withdrawn from the bone tunnels in the direction of its entry.

Once the anchor 12 has been properly positioned in bone tunnel 11, a pulling force is exerted on the opposite end 43 of ligament or repair material 8 so as to firmly set barbs 36 into the cancellous region 42 of femur 4. Suture 28 may then be removed from anchor 12.

Thereafter, the other end 43 of ligament or repair material 8 may be affixed to the tibia. This may be accomplished by using another anchor 12 appropriately attached to end 43 or, alternatively, it may be attached to tibia 2 in any one of the many ways well known in the art. By way of example, if end 43 consists solely of soft tissue or tissue substitute, the soft tissue or tissue substitute may be attached to the tibia by staples, screws and the like. On the other hand, if end 43 includes a bone block, the block can be anchored in bone tunnel 10 using an interference screw. Such attachments are of the sort well known in the art.

Figure 5:
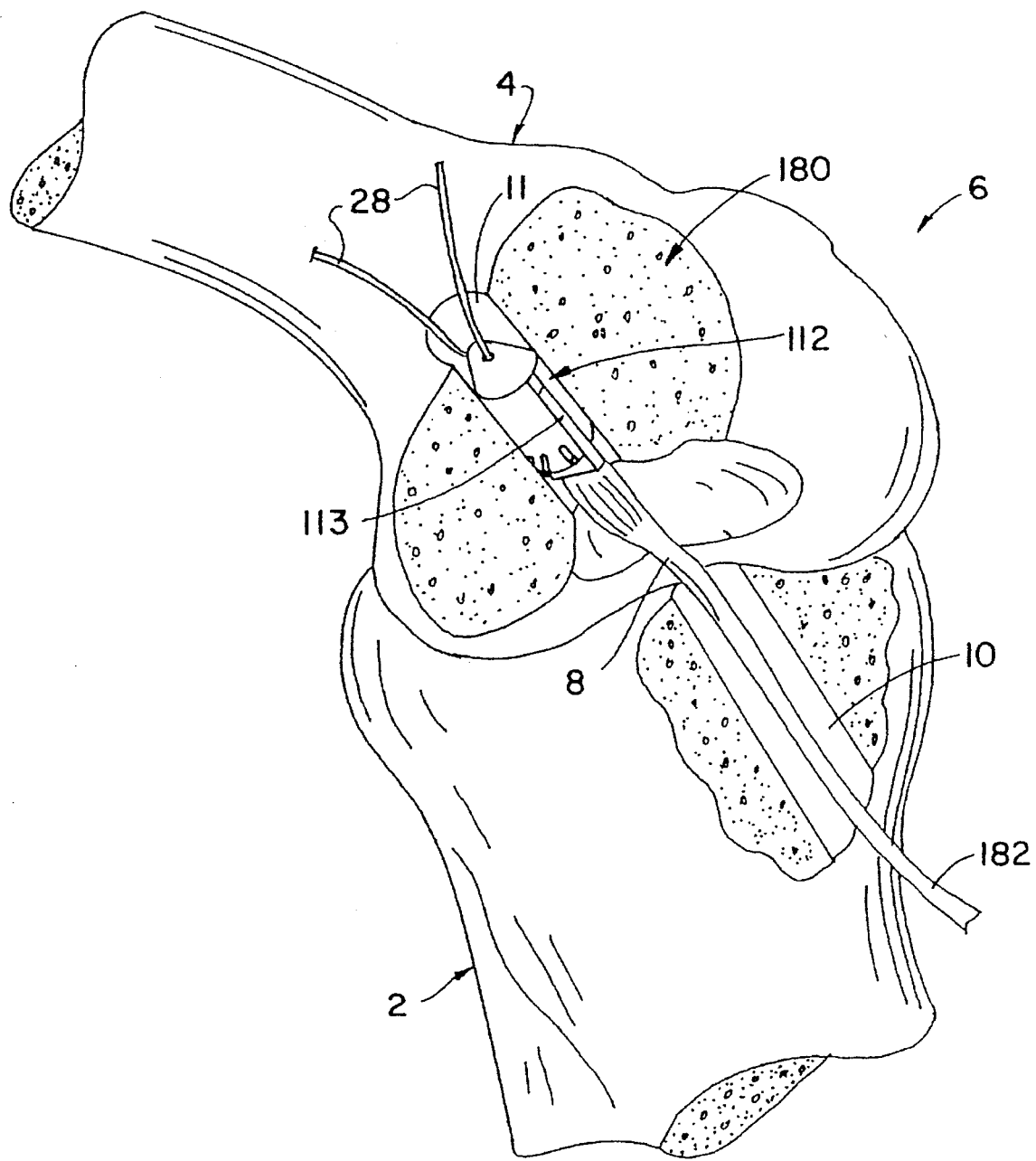
FIG. 5 is a side view similar to that of FIG. 1, but showing a second embodiment of a surgical anchor formed in accordance with the present invention, wherein the surgical anchor is attached to a bone block located at one end of a ligament.
Figure 6:
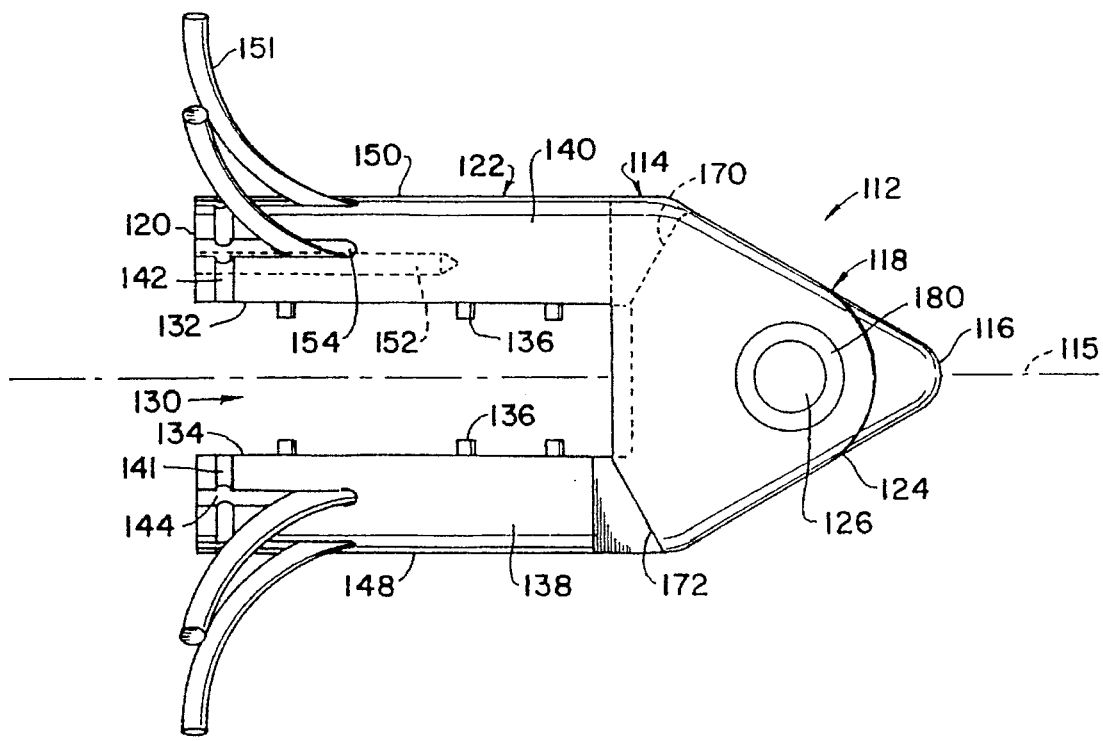
FIG. 6 is a side view of the surgical anchor shown in FIG. 5, with the anchor being shown in its closed position.

Referring next to FIG. 5, there is shown a surgical anchor 112 which constitutes a second embodiment of the invention. Surgical anchor 112 is in many respects similar to the aforementioned anchor 12, although it is also different in many ways as well. More particularly, surgical anchor 112 is specifically adapted to engage and grip a bone block or plug 113 which is attached to one end of a ligament or other repair material 8, and to attach it to a bone. In FIG. 5, surgical anchor 112 is shown attaching bone block 113 to a femur 4.

Looking now at FIGS. 5–19, anchor 112 comprises a body 114, a longitudinal axis 115, a front end 116, a front portion 118 adjacent front end 116, a rear end 120, and a rear portion 122 adjacent rear end 120. The outer surface 124 of front portion 118 tapers gradually toward longitudinal axis 115 as it extends toward front end 116. This tapering provides body 114 with a generally forwardly pointed configuration. A bore 126 extends diametrically through front portion 118, perpendicular to longitudinal axis 115. Bore 126 is sized such that a strong suture 28 (FIG. 5), or some other suitable anchor pulling means, may be connected thereto for pulling anchor 112 in a forward axial direction.

Figure 9:
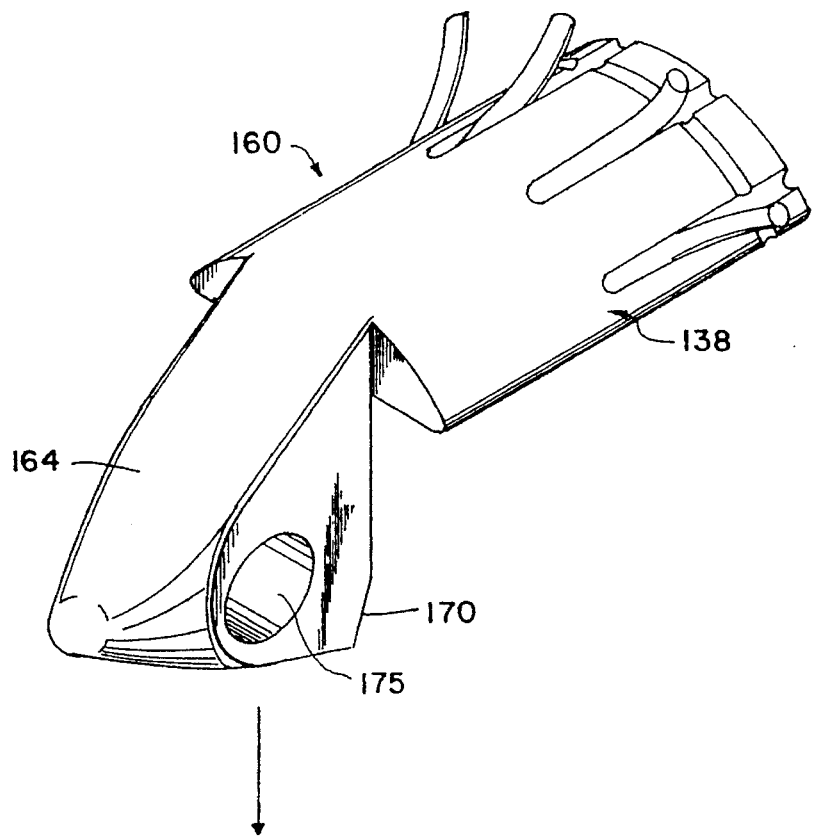
FIG. 9 is an exploded perspective view of the components forming the surgical anchor shown in FIGS. 5–8.
Figure 9:
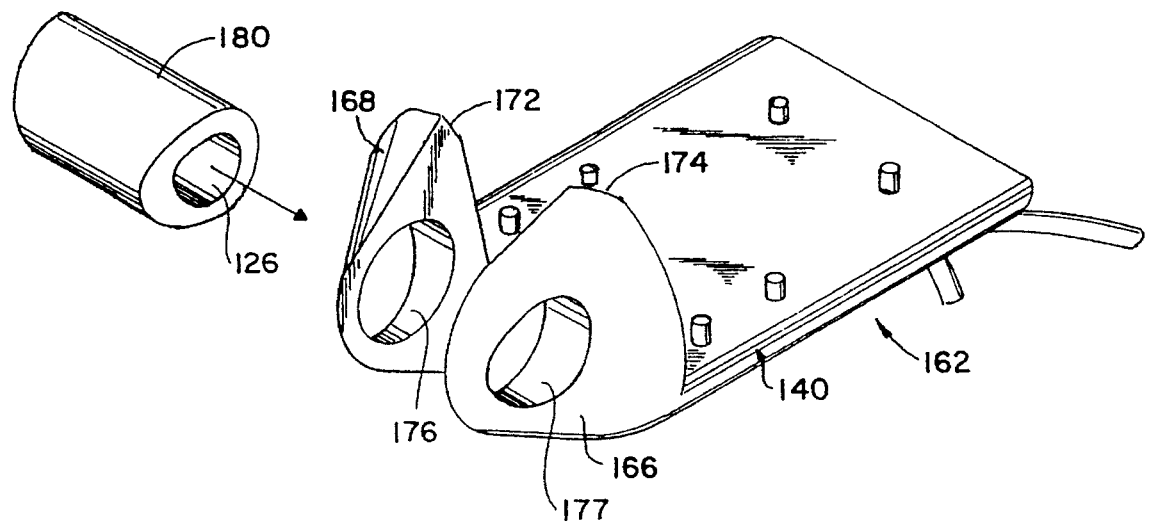

Rear portion 122 includes a diametrical slot 130 located in substantially the same plane as bore 126. Slot 130 extends forwardly from rear end 120. The opposing side walls 132 and 134 defining slot 130 each includes a plurality of inwardly extending tines 136. Tines 136 may extend into slot 130 substantially perpendicular to side walls 132 and 134 as shown, or tines 136 may extend at an acute angle to the longitudinal axis of surgical anchor 112. In the preferred embodiment, each of the side walls 132 and 134 includes six tines 136 extending into slot 130. These six barbs are arranged in three groups of two barbs each, one group adjacent each open side of the slot 130 (FIG. 9).

Figure 7:
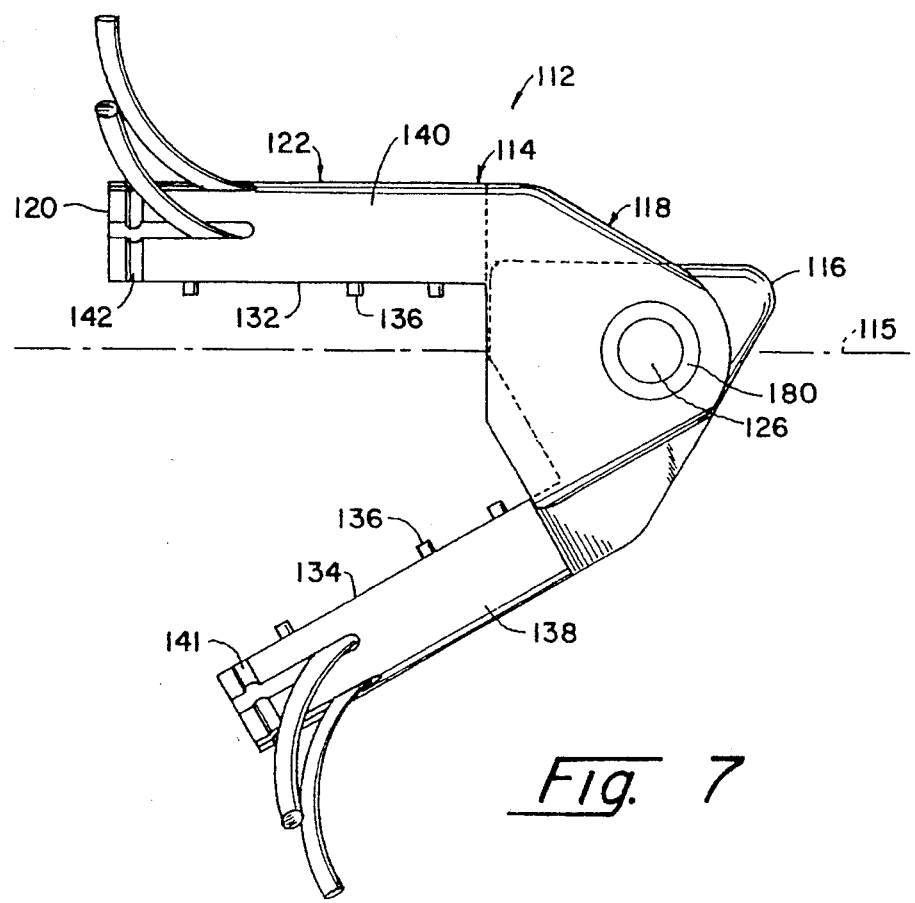
FIG. 7 is a side view of the surgical anchor of FIGS. 5 and 6, with the surgical anchor being shown in its open position.
Figure 8:
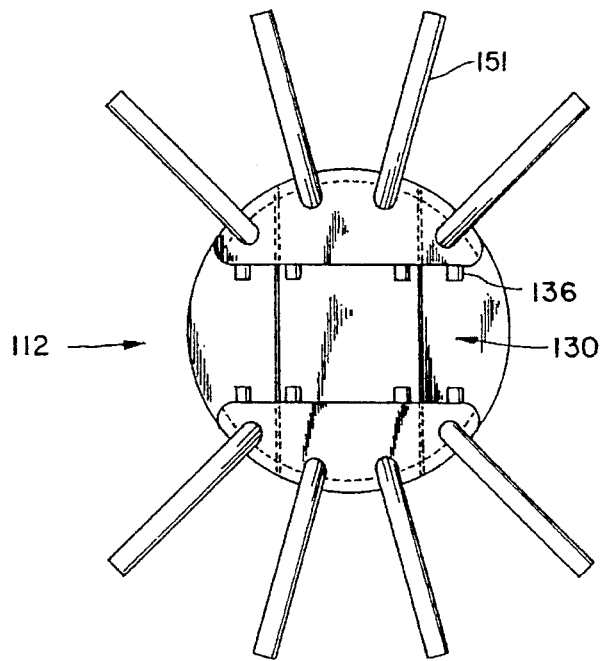
FIG. 8 is a rear view of the surgical anchor shown in FIG. 6.

Rear portion 122 is formed out of two sections 138 and 140, with the sections 138 and 140 being separated by slot 130. At least one of the sections 138 and 140 is pivotally attached to front portion 118 of body 114. In this way sections 138 and 140 can be moved between a closed position in which walls 132 and 134 confront one another in parallel, opposing relation across slot 130 (FIG. 6) and an open position in which walls 132 and 134 are moved away from one another (FIG. 7). This arrangement facilitates positioning a bone block between walls 132 and 134 for engagement by anchor 112. More specifically, when a bone block is to be positioned between the side walls 132 and 134 of slot 130, sections 138 and 140 are swung away from one another so that the anchor is in its aforementioned open position, and then the bone block is positioned between the side walls 132 and 134. Then sections 138 and 140 are swung back toward one another so that the anchor is in its aforementioned closed position, with the bone block being clamped securely between the anchor's opposing side wall surfaces 132 and 134. During use, the anchor will normally be maintained in its closed position, and the bone block thereby held by the anchor, due to the engagement of the anchor with the surrounding wall of the bone tunnel, as will hereinafter be discussed in further detail. Retention of the bone block is further enhanced by virtue of the fact that tines 136 dig into the sides of the bone block and help hold it in slot 130. In addition, circumferential grooves 141 and 142 are provided in portions 138 and 140, respectively, to permit a length of suture or other cord-like material (not shown) to be tied around rear portion 122 after a bone block has been positioned in slot 130. This suture tie will further ensure that the anchor will remain in its closed position and the bone block retained by the anchor during use.

Suture anchor 112 also comprises a plurality of longitudinal channels 144 formed in anchor sections 138 and 140. Channels 144 generally correspond to the channels 34 discussed above with respect to surgical anchor 12. It is to be appreciated, however, that in anchor 112 the channels 144 are located adjacent the anchor's rear end 120, in outer surfaces 148 and 150, respectively, of sections 138 and 140. One barb 151 extends outwardly and rearwardly from each of the channels 144. Barbs 151 are substantially the same as the barbs 36 discussed above with respect to surgical anchor 12. Bores 152 extend forwardly from the forward ends 154 of channels 144 to provide a mounting means for barbs 151, in a manner similar to the way bore 40 provide a mounting means for barbs 36 in anchor 12. It is to be appreciated that by mounting barbs 151 to, body 114 adjacent rear end 120, the engagement of barbs 151 with the surrounding bone during anchor deployment will have the effect of forcing anchor sections 138 and 140 further together, so as to ensure that the bone block will be retained by the anchor.

The specific manner in which the anchor's rear sections 138 and 140 are hinged to one another may take several forms. All of these forms are contemplated to fall within the scope of the present invention in its broadest forms. In the preferred embodiment, however, body 114 is formed in two pieces, indicated generally at 160 and 162 in FIG. 9. Piece 160 includes section 138 of rear portion 122 and a center segment 164 of front portion 118, where center segment 164 extends perpendicular to the axis of bore 126. Piece 162, on the other hand, includes section 140 of rear portion 122 and the two side segments 166 and 168 of front section 118. Side segments 166 and 168 combine with the aforementioned segment 164 to form the complete front section 118.

Pieces 160 and 162 are formed so as to allow them to rotate relative to each other about bore 126. In the embodiment shown, this is accomplished by slightly spacing portion 170 of piece 160 from the adjacent section 140, and tapering it outwardly and forwardly. At the same time, portions 172 and 174 of piece 162 are slightly spaced from the adjacent section 138, and also are tapered outwardly and forwardly.

Body 114 is assembled by sliding center segment 164 between side segments 166 and 168, in tongue-in-groove relation. In this configuration, a bore 175 in center segment 164 is aligned with bores 176 and 177 in side segments 168 and 166, respectively. Thereafter, a hollow pin 180 is inserted into bores 176, 175 and 177. The outer surface of pin 180 frictionally engages the walls of segments 168, 164 and 166 so as to hinge pieces 160 and 162 to each other. The central lumen of hollow pin 180 forms the aforementioned bore 126 which is to receive anchor pulling means 28. It will be understood that the spacing and tapering of portions 170, 172 and 174 relative to the adjoining sections 138 and 140 facilitates the pivotal movement of pieces 160 and 162 relative to each other. This is because center segment 164 is allowed to pivot freely a preselected distance about pin 180.

Selected exemplary dimensions for anchor 112 are set forth below:

| | |
|---|---|
| Length | 0.81 inches |
| Maximum Diameter | 0.40 inches |
| Width of Slot 130 (Fig. 6) | 0.170 inches |
| Length of Channels 144 | 0.180 inches |
| Length of Barbs 151 in their straight configuration | 0.28 inches |
| Diameter of Barbs 151 | 0.03 inches |
| Angular spacing between Channels 144 | 30° |
| Internal Diameter of Pin 180 | 0.08 inches |

The use of surgical anchor 112 will now be described in the context of anchoring one end of an anterior cruciate ligament 8, having a bone block 113 attached thereto, to a femur 4, as shown in FIG. 5.

A length of strong suture 28 is first threaded through bore 126 in the front portion of the anchor. If desired, the free ends of the length of suture may be secured together to facilitate grasping the free suture ends and applying a pulling force thereto. Anchor 112 is placed into its open position (FIG. 7) and the bone block 113 (affixed to the end of the ligament or other elongate soft tissue repair material 8) is located between sections 138 and 140.

As is well known in the art, the bone block 113 and ligament 8 may be a natural tissue graft harvested from elsewhere in the patient as a single graft or as several different grafts, or they may be taken wholly or partially from another donor, or they may be made up at least in part of artificial material, depending upon the situation. The bone block also may be formed, cut and/or shaved into substantially any shape desired. A box-like configuration is frequently preferred. Preferably bone block 113 is sized so that it will completely fill the anchor's slot 130 and so that the sides of the bone block will just project through the open sides of the slot, whereby the bone block will substantially engage the side wall of the bone tunnel upon anchor insertion. This facilitates assimilation of the bone block into the surrounding bone.

In any case, once bone block 113 has been located between anchor sections 138 and 140, the anchor is placed into its closed position (FIG. 6) whereby anchor surfaces 132 and 134 will grip bone block 113. Tines 136 will help hold the bone block to the anchor. A length of suture may then be tied into anchor grooves 141 and 142 to help hold the two sections of the anchor closed. Next, anchor pulling means 28 is threaded through the tibial and femoral bone tunnels 10 and 11, respectively. Thereafter, the free ends of the suture 28 is pulled so as to draw the anchor 112 (and hence its associated bone block 113 and ligament 8 as well) through tibial bone tunnel 10 and part way through femoral bone tunnel 11, until anchor 112 sits in the relatively soft cancellous region 180 in femur 4. At the same time, the free end 182 of ligament 8 will extend out of tibial bone tunnel 10, as shown in FIG. 5. It will be understood that the generally forwardly pointed configuration of the anchor will facilitate its entry into and through the bone tunnels. It will also be understood that as the anchor is pulled along the bone tunnels, the outwardly extending barbs 151 will engage the side walls of the bone tunnels, deflecting inwardly so as to allow the anchor to pass down the bone tunnels. This engagement of barbs 151 with the wall of the bone tunnels will tend to force anchor segments 138 and 140 together, thereby further ensuring that the anchor will tightly grip bone block 113 and prevent the graft from separating from the anchor. Barbs 151 will resiliently engage the surrounding bone so as to prevent the anchor from being withdrawn from the bone tunnels in the direction of its entry.

Once anchor 112 is properly positioned in bone tunnel 11, a pulling force is exerted on the opposite end 182 of ligament or repair material 8 so as to firmly set barbs 151 into the cancellous region 180 of femur 4. Suture 28 may then be removed from anchor 112.

Thereafter, the other end 182 of ligament or repair material 8 may be affixed to the tibia. This may be accomplished by using an anchor 112 appropriately attached to the end 182, if end 182 includes a bone block, or by using an anchor 12, or, alternatively, it may be attached to tibia 2 in any one of the many other ways well known in the art, e.g. by staples, screws or the like, depending on the nature of graft end 182.

Numerous variations, modifications, adjustments, alterations and alternative uses of the present invention will occur to those skilled in the art in view of the foregoing description of two exemplary and illustrative embodiments of the invention.

Thus, for example, one might use an anchor 12 or an anchor 112 in a setting other than the knee. Furthermore, one might vary the spacing and number of barbs 36 and/or barbs 151. Or one might form tines 136 with an alternative geometry. These and other changes of their type are all considered to be within the scope of the present invention in its broadest forms.

It will, therefore, be understood that this specification is intended to be illustrative only, and in no way limiting of the invention. The only limitations of the breadth and scope of this invention are set forth in the appended claims.

ADVANTAGES OF THE INVENTION

Numerous advantages are obtained by practicing the present invention.

For one thing, a surgical anchor is provided which is useful in the repair and/or replacement of ligaments, tendons and similar elongated soft tissues.

Also, a surgical anchor is provided for holding a bone block in place in a bone tunnel, so that a piece of soft tissue attached to the bone block can be connected to a bone under tension.

And the present invention provides a surgical anchor which avoids the danger of severing, twisting or otherwise damaging soft tissue repair or replacement material.

Furthermore, the present invention provides a surgical anchor which may be inserted into a tunnel formed in a bone without causing serious damage to the surrounding bone.

And a surgical anchor is provided which is adapted to hold repair or replacement material in proximity to bone in a manner which promotes the growth of a permanent attachment therebetween.

And the present invention provides a surgical anchor which may be drawn, rather than pushed, into a tunnel formed in bone.

Furthermore, the present invention provides a surgical anchor which includes simple and convenient means for attaching repair or replacement material or an object thereto.

And the present invention provides an improved method for repairing and/or replacing ligaments, tendons or similar tissue by affixing an end of such tissue (or its replacement) within a tunnel extending through a bone or bone-like structure.

What is claimed is:

1. A surgical anchor for fixedly locating a free end of a ligament, tendon or a similar elongated, non-rigid member formed from natural or artificial materials or both having a substantially rigid object attached to at least one free end thereof within a piece of bone or bone-like material defining a substantially symmetrical tunnel therein, comprising:

a body adapted for longitudinal insertion into said tunnel, and a plurality of barbs;

said body having a longitudinal axis, an outer surface, a front end, a rear end, a front portion adjacent said front end, a rear portion adjacent said rear end, connection means associated with said front portion, and attachment means associated with said rear portion, said connection means being adapted to connect said anchor to anchor pulling means, and said attachment means being adapted to connect said rigid object to said anchor, said attachment means comprising a first section of said rear portion defining a first wall and a second section of said rear portion defining a second wall, said first and second walls being located in facing parallel relation so as to together define a diametrical slot extending through said body from said rear end to said front portion, at least one of said first and said second sections being pivotally movable relative to said front portion of said body; and said barbs each comprising an outer end and an inner end, said inner end being attached to said body, and each said barb being formed and connected to said body so that said outer end is normally disposed outwardly beyond an axial projection of the maximum transverse cross-section of said body, but each said barb being elastically deformable so that said outer end may be disposed inwardly of an axial projection of the maximum transverse cross-section of said body.

2. The surgical anchor of claim 1 wherein said first and second walls each define at least one inwardly facing tine extending therefrom at an acute angle pointed in a direction substantially opposite to the direction of intended forward movement of the anchor in said tunnel.

3. The surgical anchor of claim 1 wherein said front portion of said body defines a bore extending transversely therethrough and includes a first part, a second part and a hollow pin; said hollow pin being located within said bore such that said first part and said second part are pivotally movable relative to each other about said hollow pin; and wherein each of said first and second sections of said rear portion of said body is attached to a separate one of said parts of said front portion of said body.

4. The surgical anchor of claim 1 wherein said barbs are formed of wire.

5. The surgical anchor of claim 4 wherein said wire is made of a pseudoelastic shape memory alloy.

6. The surgical anchor of claim 1 wherein said body defines a plurality of identical longitudinal channels located substantially adjacent said rear end of said body, said channels being located in circumferentially spaced relation to each other about said outer surface, each said channel including a forward end lying in the same plane transverse to said longitudinal axis; and one of said plurality of barbs extends outwardly and rearwardly from a forward end of each of said channels.

7. The surgical anchor of claim 6 wherein three of said longitudinal channels are located adjacent said rear end on the outer surface of the first and second sections of the rear portion of the body, respectively.

8. A method of affixing a rigid object attached to a free end of a ligament, tendon or similar elongate, non-rigid object formed of natural or artificial material within a piece of bone or bone-like material defining a substantially symmetrical tunnel therein, comprising the steps of:

(a) providing a body adapted for longitudinal insertion into said tunnel, and a plurality of barbs;

said body having a longitudinal axis, an outer surface, a front end, a rear end, a front portion adjacent said front end, a rear portion adjacent said rear end, connection means associated with said front portion, and attachment means associated with said rear portion, said connection means being adapted to connect said anchor to anchor pulling means, and said attachment means being adapted to connect said rigid object to said anchor, said attachment means comprising a first section of said rear portion defining a first wall and a second section of said rear portion defining a second wall, said first and second walls being located in facing parallel relation so as to together define a diametrical slot extending through said body from said rear end to said front portion, and at least one of said first and said second sections being pivotally movable relative to said front portion of said body;

said barbs each comprising an outer end and an inner end, said inner end being attached to said body, and each said barb being formed and connected to said body so that said outer end is normally disposed outwardly beyond an axial projection of the maximum transverse cross-section of said body, but each said barb being elastically deformable so that said outer end may be disposed inwardly of an axial projection of the maximum transverse cross-section of said body;

(b) connecting a length of suture or suture-like material to said connecting means;

(c) attaching said rigid object between said first and said second walls of said attachment means;

(d) threading the free ends of said suture or suture-like material through said tunnel in said bone or bone-like material; and (e) pulling on the free ends of said suture or suture-like material extending through said tunnel to thereby draw said anchor and the end of said ligament, tendon or similar elongate non-rigid object attached to said rigid object into said tunnel to a desired depth.

* * * * *